(12) United States Patent
Schwartz et al.

(10) Patent No.: US 10,111,724 B2
(45) Date of Patent: Oct. 30, 2018

(54) SURGICAL DRAPE FOR USE IN CESAREAN SECTIONS

(71) Applicants: David Schwartz, Buffalo, NY (US); David Nowicki, Lancaster, NY (US); David Power, Lancaster, NY (US)

(72) Inventors: David Schwartz, Buffalo, NY (US); David Nowicki, Lancaster, NY (US); David Power, Lancaster, NY (US)

( * ) Notice: Subject to any disclaimer, the term of this patent is extended or adjusted under 35 U.S.C. 154(b) by 374 days.

(21) Appl. No.: 14/798,761

(22) Filed: Jul. 14, 2015

(65) Prior Publication Data

US 2017/0014199 A1  Jan. 19, 2017

Related U.S. Application Data

(60) Provisional application No. 62/102,678, filed on Jan. 13, 2015.

(51) Int. Cl.
| | | |
|---|---|---|
| *A61B 46/00* | (2016.01) | |
| *A61B 46/13* | (2016.01) | |
| *A61B 46/17* | (2016.01) | |
| *A61B 46/27* | (2016.01) | |
| *A61B 46/23* | (2016.01) | |
| *A61B 46/20* | (2016.01) | |

(52) U.S. Cl.
CPC .............. *A61B 46/30* (2016.02); *A61B 46/00* (2016.02); *A61B 46/13* (2016.02); *A61B 46/17* (2016.02); *A61B 46/27* (2016.02); *A61B 46/40* (2016.02); *A61B 2046/205* (2016.02); *A61B 2046/236* (2016.02)

(58) Field of Classification Search
CPC ......... A61B 46/00; A61B 46/30; A61B 46/13; A61B 46/17; A61B 46/20; A61B 46/23; A61B 46/27; A61B 46/40; A61B 42/00; A61B 42/20; A61B 2046/201; A61B 2046/205; A61B 2046/236; A01K 23/005; A61D 1/08
See application file for complete search history.

(56) References Cited

U.S. PATENT DOCUMENTS 3,799,161 A * 3/1974 Collins ................. A61B 46/00
                                                   128/854
4,119,093 A * 10/1978 Goodman ............. A61B 46/27
                                                   128/856

(Continued)

*Primary Examiner* — Alireza Nia
*Assistant Examiner* — Rachel Berezik
(74) *Attorney, Agent, or Firm* — Vincent G. LoTempio; Kloss, Stenger & LoTempio; David T. Stephenson

(57) ABSTRACT

A surgical drape allows access to a vaginal area during cesarean sections without breaking a sterile field. The drape comprises a base sheet defined by an incision panel that overlays a peritoneal region, where the cesarean section primarily occurs; and a vagina panel that overlays a vaginal area. The incision panel has a transparent polymer film panel for viewing the incision. A collection pouch catches bodily fluids. The vagina panel enables sterile manipulation of the vagina while performing the cesarean section. The vagina panel is defined by a viewing pane for viewing the vaginal region through the base sheet. A sleeve extends through a hole in the viewing pane to manipulate the vaginal region and a baby. The sleeve is configured to allow insertion of a hand through an open end, and then manipulate the vaginal region with a closed end without breaking a sterile field.

17 Claims, 7 Drawing Sheets

(56) References Cited

U.S. PATENT DOCUMENTS

| | | | | |
|---|---|---|---|---|
| 4,196,723 | A * | 4/1980 | Moose, Jr. | A61B 46/00 128/854 |
| 4,489,720 | A * | 12/1984 | Morris | A61B 46/00 128/853 |
| 4,903,710 | A * | 2/1990 | Jessamine | A61B 46/30 128/846 |
| 5,161,544 | A * | 11/1992 | Morris | A61B 46/00 128/849 |
| 7,305,991 | B2 * | 12/2007 | Santilli | A61B 46/30 128/849 |
| 8,011,371 | B2 * | 9/2011 | Rotolo | A61B 46/00 128/849 |
| 8,641,694 | B2 * | 2/2014 | Price | A61F 5/44 128/849 |
| 2004/0103904 | A1 * | 6/2004 | Auerbach | A61B 46/27 128/856 |
| 2011/0030703 | A1 * | 2/2011 | Chua | A61B 46/27 128/856 |
| 2011/0297164 | A1 | 12/2011 | Strauch | |
| 2013/0104909 | A1 | 5/2013 | Barrier | |
| 2013/0112211 | A1 * | 5/2013 | Power | A61B 19/08 128/853 |
| 2015/0359596 | A1 * | 12/2015 | Jarrelle | A61B 46/00 128/854 |

* cited by examiner

SURGICAL DRAPE FOR USE IN CESAREAN SECTIONS

FIELD OF THE INVENTION

This application claims the benefit of U.S. Provisional Application No. 62/102,678, filed on Jan. 13, 2015. The present invention relates generally to a surgical drape for use in cesarean sections. And more particularly, pertains to surgical drapes for use during cesarean section procedures that allows medical personnel to manipulate the baby into position for cesarean section access without compromising the sterile field.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Typically, medical drapes are used in operating rooms and other departments throughout healthcare facilities for various purposes, including for use in cesarean sections. The main purpose of the medical drapes is to provide a sterile field around the surgical site and to cover the patient during an invasive procedure. Typical surgical drapes have an opening or window at the site of the actual procedure, commonly known in the medical field as a "fenestrated incision site."

Medical drapes are intended to maintain a sterile field around a fenestrated incision site, maintaining a barrier that minimizes the passage of microorganisms between the non-sterile and sterile areas. Fenestrated medical drapes are commonly made of disposable nonwoven fabrics, plastic polymeric film or perforated papers all of which surround the incision site.

Current problems with medical drapes occur in the context of cesarean sections when it becomes necessary to manipulate a baby during the procedure. The sterile fenestrated incision site is located at the uterus, but it often becomes necessary to access the vaginal region in order to manipulate the baby during the procedure.

At present, accessing the vaginal region requires intervention by medical personnel, wherein someone must break the sterile field and move themselves into the non-sterile area, away from the sterile fenestrated incision site. This process can be time-consuming, as it requires the doctors and nurses involved in the procedure to reapply sleeves and surgical gowns each time the sterile field is broken. Further, it exposes the involved medical personnel to bodily fluids and non-sterile surgical areas. Recurrent breaks in the sterile field can also increase the risk of post-operation patient infection.

It is readily apparent that there is a long-felt need for a surgical drape which allows for access to the vaginal region during a cesarean section operation without breaking the sterile field of the fenestrated incision site.

The present invention seeks to alleviate the problems associated with sterility during cesarean section operations and provide a device that maintains a sterile field while still allowing medical personnel to manipulate the baby when necessary during such operations.

SUMMARY OF THE INVENTION

It is the object of the disclosure to provide a surgical drape that covers a patient for protection during a cesarean section. The surgical drape of the present disclosure is comprised of various components for different uses in the operating room. In one embodiment, the surgical drape is defined by a base sheet. The base sheet has an overall appearance consisting of a large rectangular piece of non-woven base sheet with an absorbent reinforcement pad in the center and a fenestration cut within the pad.

The base sheet comprises an incision panel where the cesarean section primarily occurs, and where a baby is delivered. The base sheet further includes a vaginal panel that is disposed approximately over the vaginal area. The vaginal panel enables sterile manipulation of the vagina and possible the baby while performing the cesarean section. The incision panel and the vaginal panel are separated by an approximate distance to where the uterus and the vagina are disposed on a patient. A sleeve integrates into the vaginal panel to enable manipulation of the vaginal region and a baby, if necessary. The vaginal panel includes a viewing pane to enable visibility of the vaginal manipulations.

The incision panel comprises a polymer film panel that is transparent and has an approximately eighteen 18" clear plastic viewing area. In this manner, the peritoneal region, where the incision occurs, is visible through the incision panel. The incision panel further includes a collection pouch that forms a perimeter around the polymer film panel. The collection pouch includes a closable opening for receiving superfluous bodily fluids that overflow from the peritoneal region of the patient. In one embodiment, the collection pouch is a clear polyethylene pouch configured for collection of bodily fluids. The collection pouch seals to the peritoneal region during surgery. Though, a bendable wire may also be used to hold the collection pouch securely over the polymer film panel.

The other major component of the base sheet is the vaginal panel. The vaginal panel positions approximately over a vaginal region. The vaginal panel includes an outer surface made of a flexible, nonlatex material. The vaginal panel further includes and an inner surface that engages the vaginal region, which is fabricated from a knitted, nylon material. The vaginal panel has an open area. The open area is filled with a substantially transparent viewing pane. The viewing pane enables viewing of the vaginal region.

A sterile sleeve is integrated into the viewing pane. The sleeve enables a hand to penetrate the vaginal region, and manipulate the vagina, and a baby if necessary. The sleeve completely covers the hand during this manipulative process. The viewing pane has a generally concentrically disposed hole that enables the sleeve to penetrate the vaginal region.

Because the vaginal panel is not removed from the patient while the sleeve is manipulating the vaginal region, and because the hand is completely covered, a sterile environment of the peritoneal region is not broken, and thereby the integrity of the cesarean section is maintained. For example, the sleeve allows medical personnel to reach down to access the vaginal region during cesarean section operations without exposing the peritoneal region or the vaginal region to air or direct contact from a medical personnel's skin.

The sleeve is defined by an open end that enables insertion of a hand, and a closed end that forms the terminus, where manipulation of the vaginal region chiefly occurs. The closed end of the sleeve may include a glove with fingers or a closed mitten configuration. The viewing pane allows the medical personnel to view the closed end of the sleeve through the vaginal panel while operating the sleeve.

The sleeve is stored in a folded position inside the concentrically disposed hole of the viewing pane. This provides a sterile environment for the sleeve while in the folded position. The sleeve may be secured into the folded position with a fastening member. The fastening member may include a paper strip having an adhesive on one side. Removing the fastening member and unfolding the sleeve enables the sleeve to extend into the vaginal region.

It is one object of the disclosure to provide a viewing pane covering a large area of the vaginal panel made of clear plastic material, through which medical personnel can view the vaginal region as needed during the cesarean section procedure.

It is another objective to collect bodily fluids that overspill from the incision panel with a collection pouch.

It is another objective to simultaneously manipulate the vaginal region and deliver a baby from the peritoneal region without breaking the sterile environment of the regions covered by the surgical drape.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1:
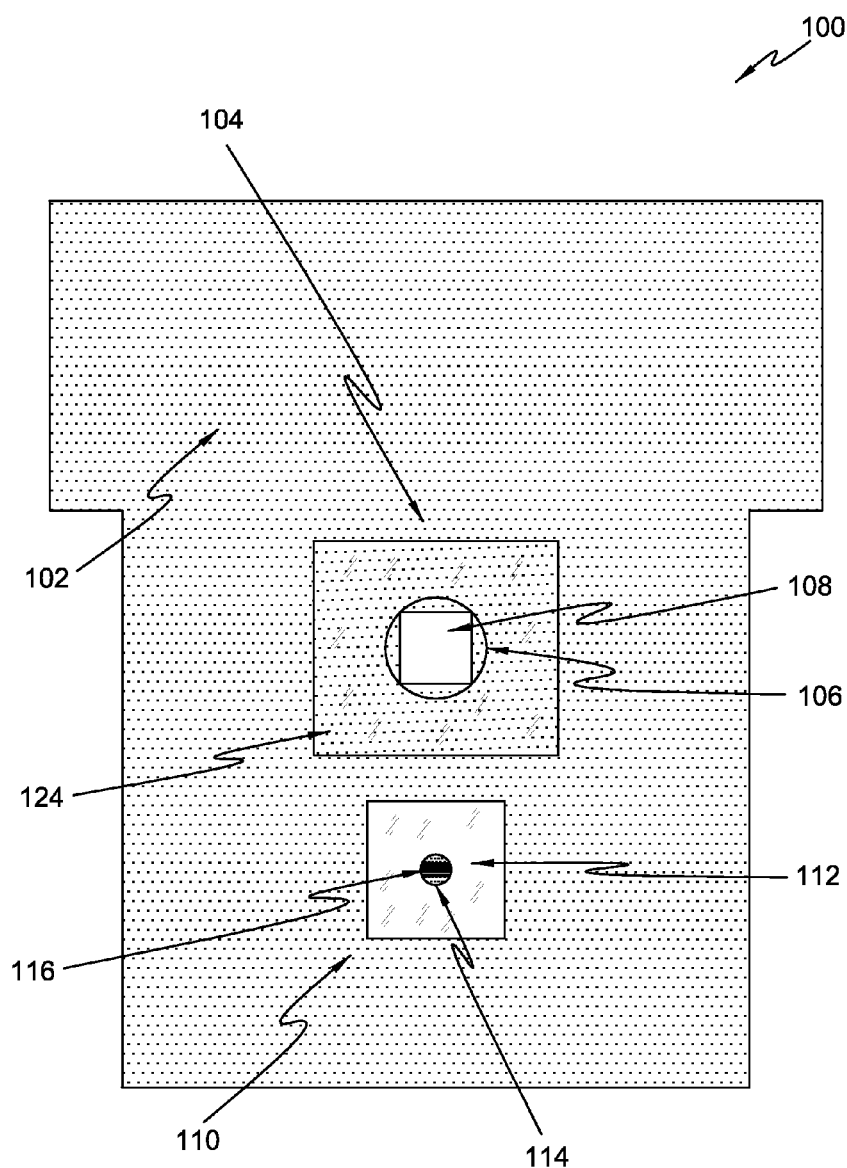
FIG. 1 is a top view of an exemplary surgical drape.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

The present disclosure, referenced in FIGS. 1-10, illustrates a surgical drape 100 for use in cesarean sections. Surgical drape 100 seeks to alleviate the problems associated with sterility during cesarean section operations. Surgical drape 100 maintains a sterile field while still allowing a medical professional to simultaneously manipulate a vaginal area and/or a baby during the cesarean section operation.

As illustrated in FIG. 1, a surgical drape 100 comprises a base sheet 102. Base sheet 102 at least partially covers a patient 122 for protection during a cesarean section. Base sheet 102 is defined by an incision panel 104 where the cesarean section primarily occurs, and where a baby is delivered. Base sheet 102 further includes a vaginal panel 110 that is disposed approximately over a vaginal region of patient 122. Vaginal panel 110 enables sterile manipulation of the vaginal region, and possible the baby, while still performing the cesarean section on the incision panel 104. Incision panel 104 and vaginal panel 110 are separated by an approximate distance from where the uterus and the vagina are disposed on a patient 122.

Figure 2:
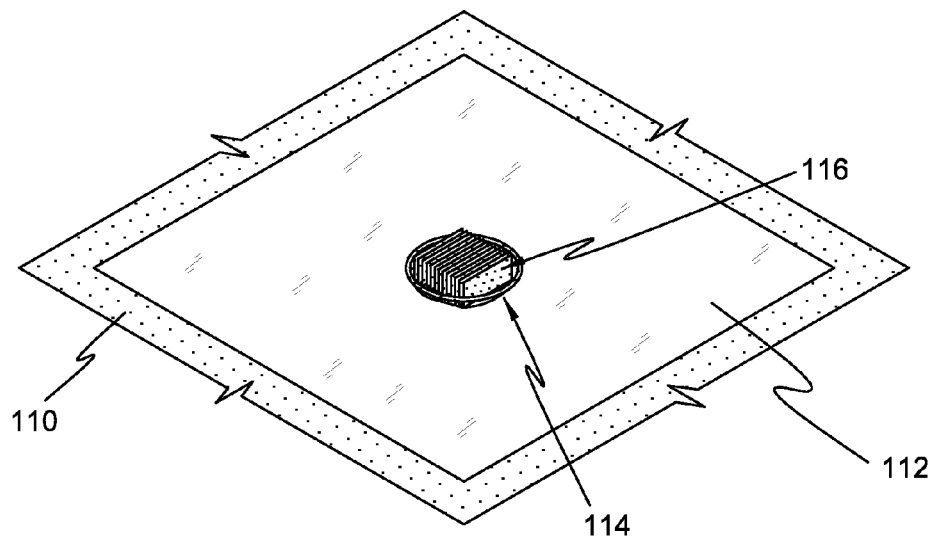
FIG. 2 is a top perspective view of the surgical drape with an exemplary sleeve in a folded position.

As referenced in FIG. 2, base sheet 102 of surgical drape 100 may have an overall appearance consisting of a large rectangular piece of non-woven panel with an absorbent reinforcement pad in the center. In some embodiments, base sheet 102 may be fabricated of commonly used medical drape material such as SMS (Spunbond-Meltblown-Spunbond) material, or spunlace material, wherein both materials are a type of non-woven fabric.

Figure 3:
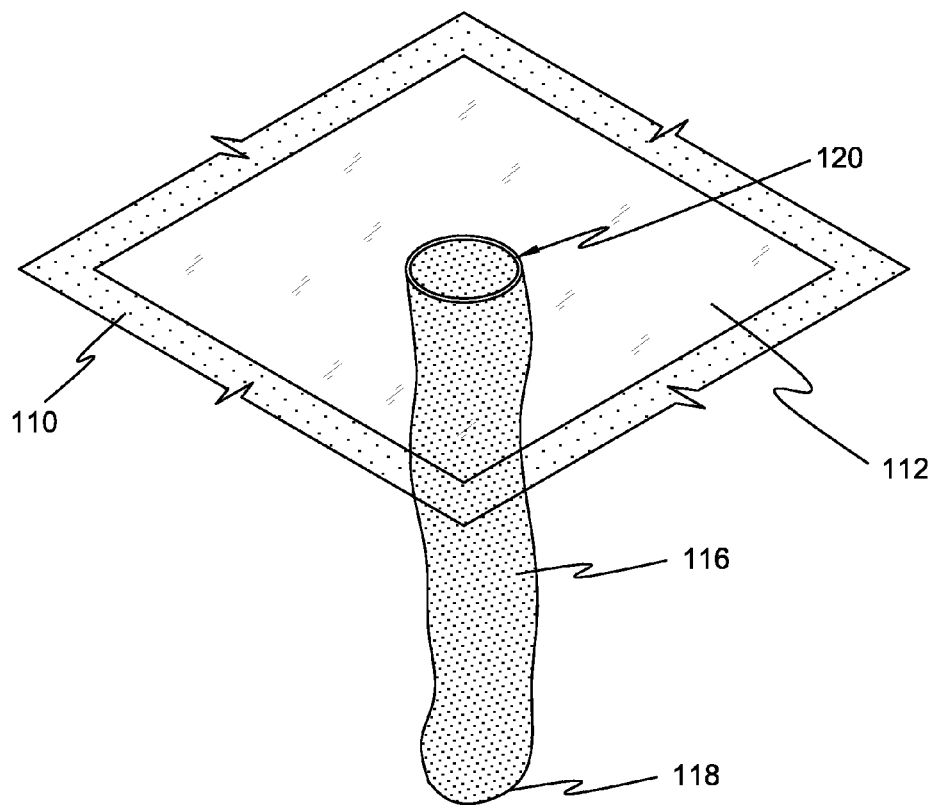
FIG. 3 is a top perspective view of the surgical drape with an exemplary sleeve in an extended position.

Looking at FIG. 3, base sheet 102 comprises an incision panel 104 and a vaginal panel 110. Incision panel 104 is disposed approximately over the peritoneal region, or where the incision for the cesarean section occurs. In the present disclosure, incision panel 104 is surrounded by an incision tape that secures incision panel 104 to the peritoneal region of a patient 122.

Figure 4:
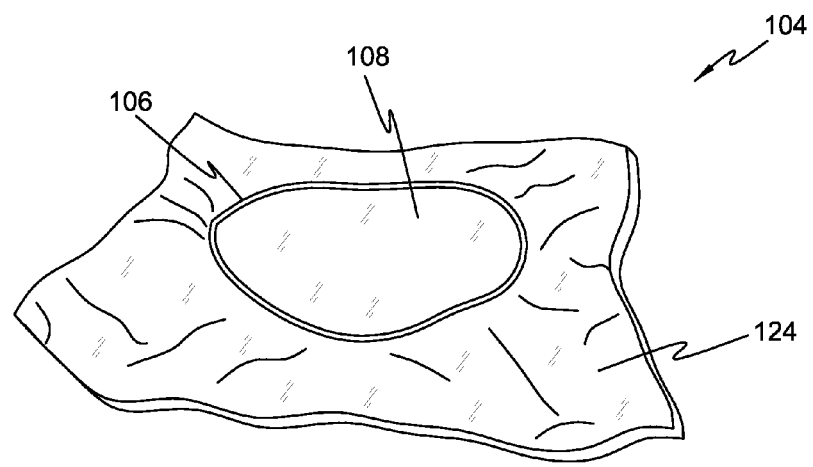
FIG. 4 is a perspective view of an exemplary incision panel.

Turning now to FIG. 4, incision panel 104 comprises a polymer film panel 108 that is transparent and has an approximately eighteen 18" clear plastic viewing area. In this manner, the peritoneal region, where the incision occurs is visible through incision panel 104.

Incision panel 104 further includes a collection pouch 124 that forms a perimeter around polymer film panel 108. Collection pouch 124 includes an opening for receiving superfluous bodily fluids that overflow from the peritoneal region of patient 122 during the cesarean section. In one embodiment, collection pouch 124 is a clear polyethylene material that is configured for collection of bodily fluids. Collection pouch 124 seals to the peritoneal region during the cesarean section. A wire 106 may be used to fasten collection pouch 124 securely over polymer film panel 108. Wire 106 may be generally circular and sufficiently malleable so as to bend to a desired shape.

Vaginal panel 110 positions approximately over a vaginal region of patient 122. Vaginal panel 110 includes an outer surface made of a flexible, non-latex material. The vaginal panel further includes an inner surface that engages the vaginal region. The inner surface may be fabricated from a knitted, nylon material. Vaginal panel 110 has an open area on which a substantially transparent viewing pane 112 overlays. Viewing pane 112 enables viewing of the vaginal region. In one embodiment, the dimension of viewing pane 112 is approximately 24" by 24". Though other dimensions may be used, depending on the size and shape of patient 122.

Sleeve 116 is integrated into viewing pane 112. Sleeve 116 enables a hand to penetrate the vaginal region, and perform various manipulations that are operatively correspond to the incision and cesarean related operations performed at incision panel 104. Sleeve 116 completely covers the hand during this manipulative process. Viewing pane 112 has a generally concentrically disposed hole 114 that enables sleeve 116 to penetrate the vaginal region. Sleeve 116 may operate through hole 114, or may be folded and stowed in hole 114, as needed.

Sleeve 116 is defined by an open end 120 that enables insertion of a hand, and a closed end 118 that forms the terminus, where manipulation of the vaginal region chiefly occurs. Closed end 118 of sleeve 116 may include a glove with fingers or a closed mitten configuration. The viewing pane allows the medical professional to view closed end 118 of the sleeve 116 through viewing pane 112 while manipulating sleeve 116. In one embodiment, the sleeve is fabricated from a Kraton™ thermoplastic rubber sheeting material. However, in other embodiments, any sterile material used in the medical field may be used.

During use of sleeve 116, an inside surface of sleeve 116 remains sterile and an outside area facing the patient 122 is unsterile. Sleeve 116 is used primarily to allow a medical professional to remain sterile while gaining entry into an unsterile area by the vagina during a delivery through a cesarean section. By using sleeve 116 the medical professional's hand avoids contamination when working below base sheet 102.

Figure 5:
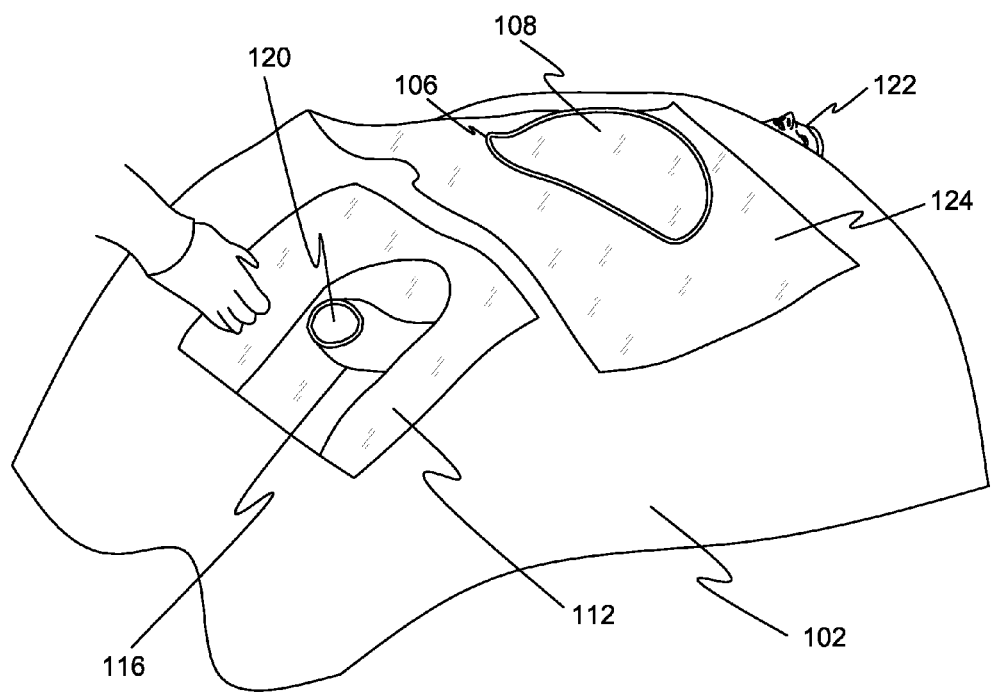
FIG. 5 is a perspective view of the surgical drape showing the intended placement on the abdominal area of a patient immediately prior to use.

FIG. 5 is a perspective view of surgical drape 100 showing the intended placement on an abdominal area of patient 122 immediately prior to use. Patient 122 is shown underneath base sheet 102 with sleeve 116 positioned distal to the vaginal region between the legs of patient 122. Viewing pane 112 allows the medical professional to observe the position of closed end 118 of sleeve 116 without having to move base sheet 102 or place the hand beneath surgical drape 100.

Figure 6:
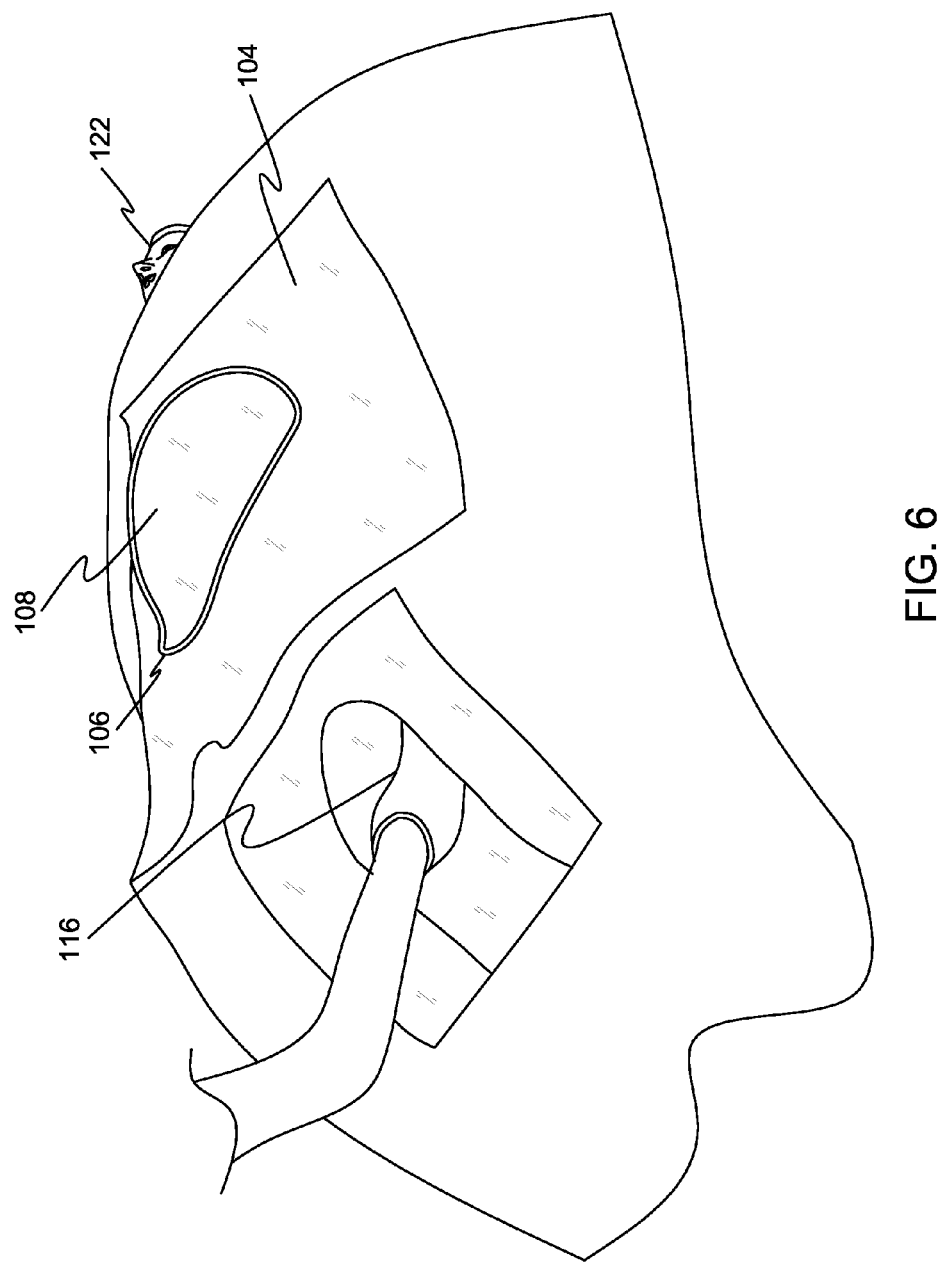
FIG. 6 is a perspective view of the surgical drape actually placed on a patient and in use.

FIG. 6 is a perspective view of surgical drape 100 actually placed on a patient 122 and in use. The hand of the medical professional is inserted into sleeve 116. Because vaginal panel 110 is not removed from patient 122 while sleeve 116 is manipulating the vaginal region, and because the hand is completely covered, a sterile environment of the peritoneal region is not broken, and thereby the integrity of the cesarean section is maintained.

For example, sleeve 116 allows medical personnel to reach down to access the vaginal region during cesarean section operations without exposing the peritoneal region or the vaginal region to air or direct contact form a medical professional's skin. In this manner, the incision and the manipulation of the vaginal region may be performed simultaneously without breaking the sterile field of surgical drape 100.

Sleeve 116 is stored in a folded position inside a concentrically disposed hole 114 of the viewing pane 112. This provides a sterile environment for the sleeve 116 while in a folded position. The sleeve 116 may be secured into the folded position with a fastening member 126. Fastening member 126 may include a paper strip having an adhesive on one side. Though other fastening means may be used in other embodiments. Removing the fastening member 126 and unfolding the sleeve 116 enables the sleeve 116 to extend into the vaginal region.

Figure 7:
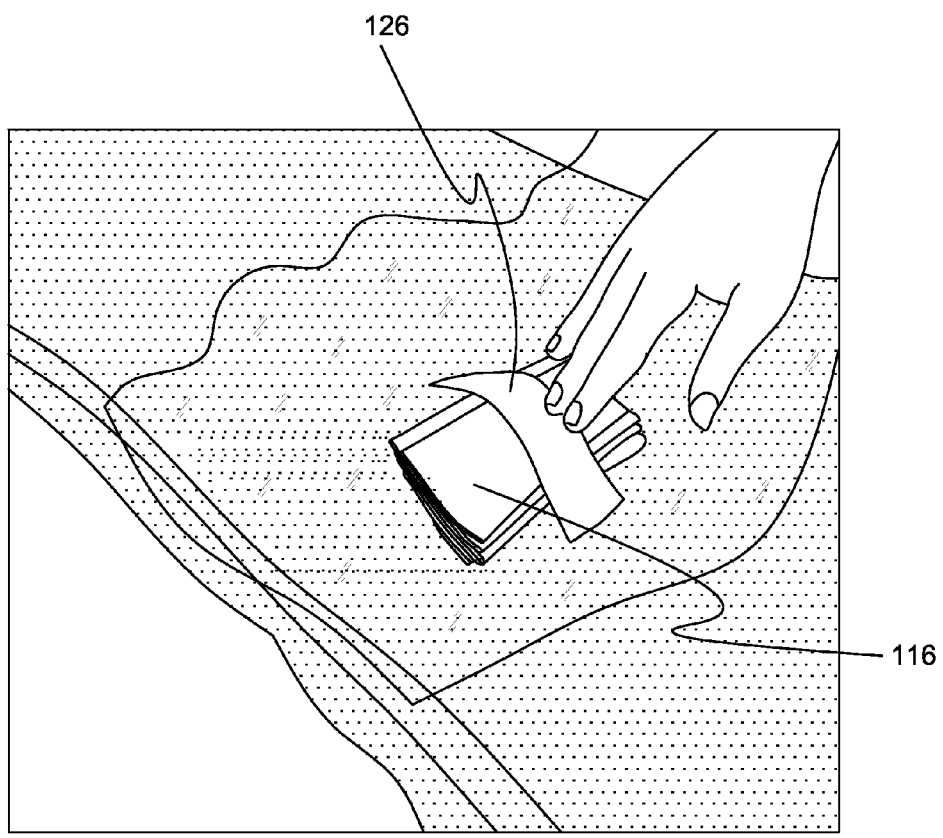
FIG. 7 is a perspective view of the sleeve prior to use in a fan-folded state.

FIGS. 3 and 4 illustrate both top and bottom views of sleeve 116 unfolded and ready for use. The sleeve 116 shown in this embodiment is a general rectangular sleeve 116 shape. FIG. 7 is a top view of sleeve 116 prior to use in a fan-folded position. Removable fastening member 126 is placed over sleeve 116 until such time that it becomes necessary to extend sleeve 116 in order to manipulate the vaginal region and the baby during the cesarean section procedure. At that time, the perforation on removable fastening member 126 is torn and sleeve 116 is put into use.

The fan-folded position is the preferred state of sleeve 116 prior to use, however it should be apparent to those skilled in the art that modifications and variations may be made to the technique of folding sleeve 116 without departing from the spirit and scope of the invention. In one alternative embodiment, sleeve 116 folds in a telescopically-folded position.

Figure 8:
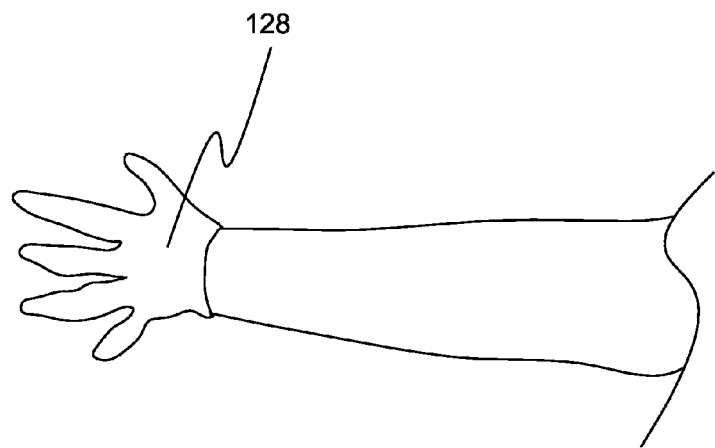
FIG. 8 is a side view of the sleeve with the closed end configured in an exemplary glove with fingers.
Figure 9:
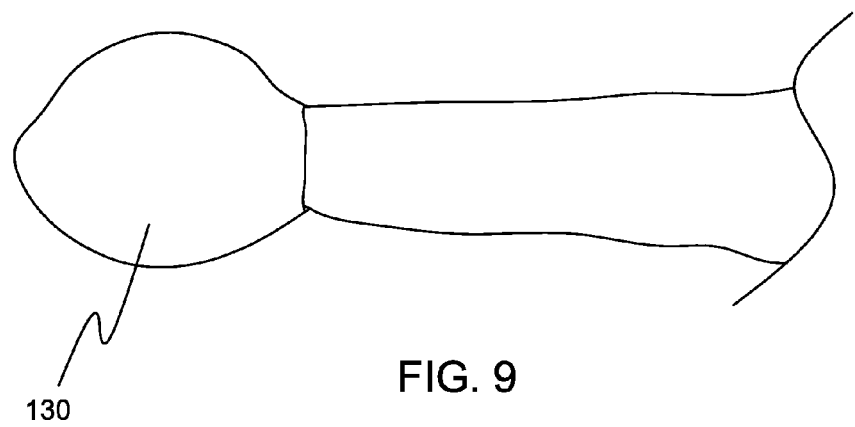
FIG. 9 is a side view of the sleeve with the closed end configured in an exemplary closed mitten.

In other embodiments of the invention, as shown in FIGS. 8 and 9 closed end 118 of sleeve 116 is made in the shape of a mitten with fingers. Though FIG. 9 illustrates sleeve 116 made in the shape of a bag with no fingers. For example, FIG. 8 shows a top view of the extended surgical sleeve 116 with closed end 118 in the general shape of a glove with fingers 128. The fingers enable flexibility and dexterity during manipulation of the vaginal region or the baby.

FIG. 9 is a top view of extended sleeve 116 with the end in the general shape of a closed mitten 130. In some embodiments, not having individual fingers on closed end 118 may be preferable. It should be appreciated that the glove with fingers 128, closed mitten 130, and suitable shapes other than those outlined can be used in the manufacture of the invention, as there are multiple embodiments that allow medical personnel/doctors to remain sterile while gaining entry into the vaginal region during a cesarean section procedure.

Figure 10:
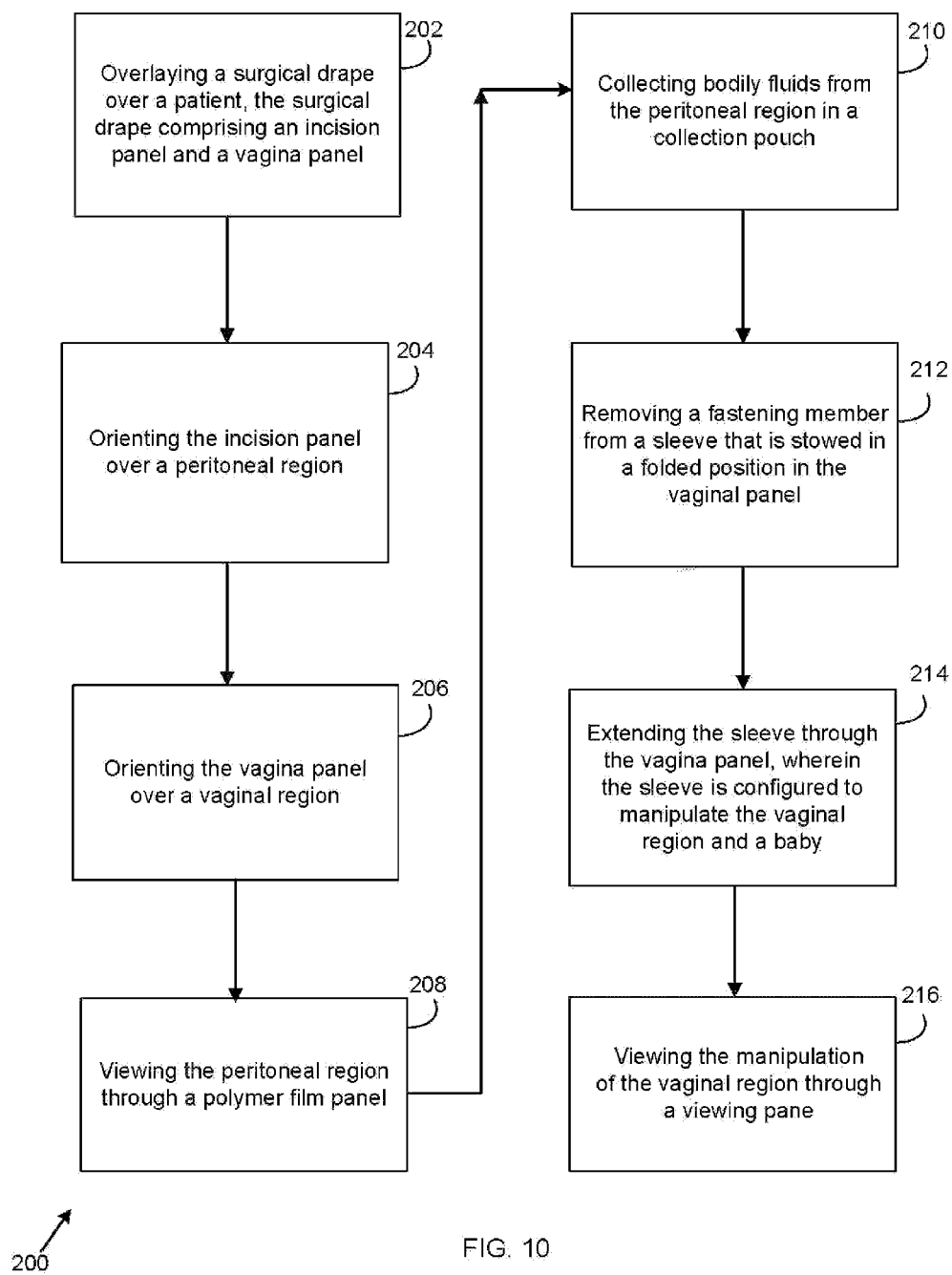
FIG. 10 is a flowchart diagram of an exemplary method for allowing access to a patient's vaginal area during cesarean sections with a surgical drape.

FIG. 10 illustrates a flowchart diagram of an exemplary method 200 for allowing access to a patient's 122 vaginal region during cesarean sections with a surgical drape 100. Method 200 comprises an initial Step 202 of overlaying a surgical drape 100 over a patient 122, the surgical drape 100 comprising an incision panel 104 and a vaginal panel 110.

The base sheet 102 covers a patient 122 for protection during a cesarean section. Base sheet 102 is defined by an incision panel 104 where the cesarean section primarily occurs, and where a baby is delivered.

In some embodiments, base sheet 102 may further include a vaginal panel 110 that is disposed approximately over the vaginal area. Vaginal panel 110 enables sterile manipulation of the vagina and possible the baby while performing the cesarean section. Incision panel 104 and vaginal panel 110 are separated by an approximate distance to where the uterus and the vagina are disposed on a patient 122.

A Step 204 may include orienting the incision panel 104 over a peritoneal region. Incision panel 104 comprises a transparent polymer film panel 108. In this manner, the peritoneal region, where the incision occurs is visible through incision panel 104. The incision panel 104 further includes a collection pouch 124 for receiving superfluous bodily fluids that overflow from the peritoneal region of patient 122.

In some embodiments, the method 200 may include a Step 206 of orienting the vaginal panel 110 over a vaginal region. Vaginal panel 110 enables sterile manipulation of the vagina while performing the cesarean section. Vaginal panel 110 is defined by a viewing pane 112 for viewing the vaginal region through the base sheet 102.

A Step 208 comprises viewing the peritoneal region through a polymer film panel 108. Polymer film panel 108 may be transparent and have an approximately eighteen 18" clear plastic viewing area. An additional Step 210 includes collecting bodily fluids from the peritoneal region in a collection pouch 124. Collection pouch 124 has a closable opening that receives the bodily fluids. In some embodiments, a Step 212 comprises removing a fastening member 126 from a sleeve 116 that is stowed in a folded position in the vaginal panel. Sleeve 116 extends through a hole 114 in viewing pane 112 to manipulate the vaginal region and a baby. Sleeve 116 is defined by an open end 120 and a closed end 118.

A Step 214 may include extending sleeve 116 through the vaginal panel 110, wherein the sleeve 116 is configured to manipulate the vaginal region and a baby. Sleeve 116 is configured to allow insertion of a hand through an open end 120, and then manipulate the vaginal region with a closed end 118 without breaking a sterile field.

A final Step 216 comprises viewing the manipulation of the vaginal region through a viewing pane 112. Closed end 118 may be configured as a glove with fingers or a closed mitten for manipulation of the vaginal region and a baby. In this manner, the incision and the manipulation of the vaginal region may be performed simultaneously without breaking the sterile field of surgical drape 100.

Although the invention has been described with reference to certain preferred embodiments, it will be appreciated by those skilled in the art that modifications and variations may be made without departing from the spirit and scope of the invention. It should be understood that applicant does not intend to be limited to the particular details described above and illustrated in the accompanying drawings.

What I claim is:

1. A surgical drape for allowing access to a patient's vagina area during cesarean sections, the drape comprising:
   a base sheet, the base sheet configured to enable covering of a peritoneal region and a vaginal region;
   an incision panel, the incision panel defined by a polymer film panel, a collection pouch, and a wire, the incision panel configured to overlay the peritoneal region, the polymer film panel configured to be transparent for enabling viewing of the peritoneal region, the wire configured to help fasten the collection pouch to the polymer film panel;
   a vagina panel, the vagina panel defined by a viewing pane, the viewing pane having a hole, the viewing pane configured to be transparent for enabling viewing of the vaginal region, the viewing pane disposed adjacent to the vagina panel; and
   a sleeve, the sleeve defined by a closed end and an open end, the sleeve disposed to join with the vagina panel, the closed end of the sleeve configured to pass through the hole in the viewing pane for manipulation of the vaginal region, wherein the sleeve is folded into folds for stowage in the hole of the viewing pane; wherein the sleeve is secured within the hole with an adhesive tape; wherein the adhesive tape is attached to the sleeve prior to being removed from the sleeve, and the adhesive tape is attached to an upper portion of the viewing pane, wherein the sleeve is operatively arranged to be extended toward a vaginal region by unfolding the sleeve to enable manipulation of the vaginal region without breaking a sterile field.

2. The drape of claim 1, wherein the drape is configured to cover a patient during a cesarean section.

3. The drape of claim 1, wherein the base sheet is fabricated from a nonwoven SMS material.

4. The drape of claim 1, wherein the incision panel is fabricated from a thermoplastic polymer.

5. The drape of claim 1, wherein the collection pouch of the incision panel is fabricated from polyurethane.

6. The drape of claim 1, wherein an opening of the collection pouch is configured to receive overflow of a bodily fluid from the peritoneal region.

7. The drape of claim 1, wherein the wire is a bendable wire.

8. The drape of claim 1, wherein the viewing pane of the vagina panel is fabricated from clear polyethylene.

9. The drape of claim 1, wherein the hole is concentrically disposed in the viewing pane.

10. The drape of claim 1, wherein the open end of the sleeve is configured to enable insertion of a hand for manipulation of the vaginal region and a baby.

11. The drape of claim 1, wherein the sleeve is fabricated from a thermoplastic rubber sheeting material.

12. The drape of claim 1, wherein the closed end of the sleeve forms a glove with fingers or a closed mitten.

13. The drape of claim 1, wherein the sleeve is secured with a fastening member.

14. The drape of claim 13, wherein the fastening member is a paper strip with an adhesive.

15. The drape of claim 14, wherein the fastening member is configured to fasten the sleeve to the viewing pane while the sleeve is folded.

16. A surgical drape for allowing access to a patient's vagina area during cesarean sections, the drape comprising:
    a base sheet, the base sheet configured to enable covering of a peritoneal region and a vaginal region;
    an incision panel, the incision panel defined by a polymer film panel, a collection pouch, and a wire, the incision panel configured to overlay the peritoneal region, the polymer film panel configured to be transparent for enabling viewing of the peritoneal region, the wire configured to help fasten the collection pouch to the polymer film panel;
    a vagina panel, the vagina panel defined by a viewing pane, the viewing pane having a hole, the viewing pane configured to be transparent for enabling viewing of the vaginal region, the viewing pane disposed adjacent to the vagina panel;

a sleeve, the sleeve defined by a closed end and an open end, the sleeve disposed to join with the vagina panel, the closed end of the sleeve configured to pass through the hole in the viewing pane for manipulation of the vaginal region, wherein the sleeve is operatively arranged to enable manipulation of the vaginal region without breaking a sterile field, the sleeve further configured to fold for stowage; and a fastening member, the fastening member configured to fasten the sleeve in the hole of the viewing pane while the sleeve is folded, wherein the sleeve is folded into folds for stowage in the hole of the viewing pane; wherein the sleeve is secured within the hole with the fastening member; wherein the fastening member is attached to the sleeve prior to being removed from the sleeve, and the fastening member is attached to the viewing pane.

17. A method for allowing access to a patient's vagina area during cesarean sections with a surgical drape, the method comprising:

overlaying a surgical drape over a patient, the surgical drape comprising an incision panel and a vagina panel;
orienting the incision panel over a peritoneal region;
orienting the vagina panel over a vaginal region;
viewing the peritoneal region through a polymer film panel;
collecting bodily fluids from the peritoneal region in a collection pouch;
removing a fastening member from a sleeve that is folded into folds and stowed in a folded position in a hole in the vaginal panel, wherein the fastening member is removably attached of the sleeve prior to being removed from the sleeve, and the fastening member is attached to a viewing pane;
extending the sleeve through the vagina panel to a vaginal region by placing a hand within the sleeve and unfolding the sleeve by extending an arm toward the vaginal region, wherein the sleeve is configured to manipulate the vaginal region and a baby; and
viewing the manipulation of the vaginal region through the viewing pane.

\* \* \* \* \*